United States Patent
Uchida

(10) Patent No.: US 12,171,577 B2
(45) Date of Patent: Dec. 24, 2024

(54) IMPLEMENT FOR POSITIONING ELECTRODES FOR 12-LEAD ELECTROCARDIOGRAM

(71) Applicant: JAPANESE ORGANIZATION FOR MEDICAL DEVICE DEVELOPMENT, INC., Tokyo (JP)

(72) Inventor: Takahiro Uchida, Tokyo (JP)

(73) Assignee: JAPANESE ORGANIZATION FOR MEDICAL DEVICE DEVELOPMENT, INC., Tokyo (JP)

( * ) Notice: Subject to any disclaimer, the term of this patent is extended or adjusted under 35 U.S.C. 154(b) by 865 days.

(21) Appl. No.: 15/734,468

(22) PCT Filed: May 30, 2019

(86) PCT No.: PCT/JP2019/021638
§ 371 (c)(1),
(2) Date: Dec. 2, 2020

(87) PCT Pub. No.: WO2019/230921
PCT Pub. Date: Dec. 5, 2019

(65) Prior Publication Data
US 2021/0236060 A1    Aug. 5, 2021

(30) Foreign Application Priority Data
Jun. 2, 2018   (JP) .................................. 2018-106546

(51) Int. Cl.
*A61B 5/00*     (2006.01)
*A61B 5/28*     (2021.01)

(52) U.S. Cl.
CPC .............. *A61B 5/6842* (2013.01); *A61B 5/28* (2021.01)

(58) Field of Classification Search
CPC ... A61B 5/6804; A61B 5/6805; A61B 5/6823; A61B 5/6841; A61B 5/283; A61B 5/274;
(Continued)

(56) References Cited

U.S. PATENT DOCUMENTS 5,995,861 A * 11/1999 Price ...................... A61B 5/282
                                                                600/382
6,850,791 B1 * 2/2005 Axelgaard ........... A61B 5/6805
                                                                600/388
(Continued)

FOREIGN PATENT DOCUMENTS

| CN | 206197144 U | 5/2017 |
| JP | 2016-158709 A | 9/2016 |
| JP | 2018-68596 A | 5/2018 |

*Primary Examiner* — Eun Hwa Kim
(74) *Attorney, Agent, or Firm* — Liang Legal Group, PLLC

(57) ABSTRACT

The purpose of the present invention is to provide an implement for positioning electrocardiographic measurement electrodes, with which it is possible to rapidly determine electrocardiographic electrode positions customized for individual patients. This implement (1) is for positioning electrocardiographic measurement electrodes, and has a plurality of holes (3, 5, 7, 9, 11, 13) corresponding to the positions of chest electrodes. The implement (1) preferably has a transparent front body section (19). The front body section (19) preferably has a plurality of cut-out holes (45). The implement (1) may have cut-out parts (47) that connect the plurality of holes.

11 Claims, 2 Drawing Sheets

(58) Field of Classification Search
CPC ....... A61B 5/271; A61B 5/273; A61B 5/6833; A61B 5/6842
See application file for complete search history.

(56) References Cited

U.S. PATENT DOCUMENTS

| | | | |
|---|---|---|---|
| 2008/0015426 A1* | 1/2008 | Sanfilippo | A61B 5/274 600/391 |
| 2010/0018377 A1* | 1/2010 | Baron | B23D 61/025 83/835 |
| 2015/0157225 A1* | 6/2015 | Gillberg | A61B 5/282 600/393 |
| 2016/0066809 A1 | 3/2016 | Luo et al. | |

* cited by examiner

IMPLEMENT FOR POSITIONING ELECTRODES FOR 12-LEAD ELECTROCARDIOGRAM

TECHNICAL FIELD

The present invention relates to an implement for positioning electrocardiographic measurement electrodes. More specifically, the present invention relates to an implement for rapidly determining positions of electrocardiographic electrodes depending on an individual patient.

BACKGROUND ART

Japanese Unexamined Patent Application Publication No. 2016-158709 describes an electrocardiographic measurement garment. The electrocardiographic measurement garment of this document has an electrode arrangement portion for arranging a plurality of measurement electrodes at predetermined positions (claim 1), and the electrode arrangement portion includes measurement electrodes corresponding to six chest electrodes based on the standard twelve-lead method (claim 6). However, the electrocardiographic measurement garment of this document gives priority to rapidity in the emergency field. In addition, since the electrode positions are fixed, it is difficult to cope with individual differences of patients disadvantageously.

CITATION LIST

Patent Documents

[Patent Document 1] Japanese Unexamined Patent Application Publication No. 2016-158709

SUMMARY OF INVENTION

Problems to be Solved by the Invention

An object of the present invention is to provide an implement for positioning electrocardiographic measurement electrodes, capable of rapidly determining positions of electrocardiographic electrodes depending on an individual patient.

Means for Solving the Problems

The problems described above can be addressed by an implement 1 for positioning electrocardiographic measurement electrodes, comprising a plurality of holes 3, 5, 7, 9, 11, and 13 corresponding to chest electrode positions. That is, instead of fixing the positions of the electrodes, holes for installing the electrodes are opened, and the electrodes are installed by using the holes as markers. Therefore, it is possible to rapidly determine the positions of the electrodes depending on an individual patient. For this purpose, each hole preferably has a diameter equal to or larger than that of the electrocardiographic electrode. However, the hole may also be smaller than the electrode. In this case, for example, the implement 1 may be used to mark (draw) a marker of the electrode position on a body surface of a patient, and the marker may be used to install the electrode.

Preferably, the implement 1 further has one or both of a clavicle marker (15a, 15b) existing in a region corresponding to a clavicle portion and a mammilla marker (17a, 17b) existing in a region corresponding to a mammilla portion. Using these markers, it is possible to install the implement at an appropriate position for a patient.

Preferably, the implement 1 further has a transparent front body section 19. When the front body has a transparent section, the implement 1 can be arranged at an appropriate position depending on a patient. Since it is only necessary to recognize a body portion through the front body section, transparency includes not only completely transparent but also semi-transparent or mesh-like fibers.

Preferably, the front body section 19 has a plurality of cut-out holes 45. Preferably, the plurality of cut-out holes 45 exist, for example, so as to surround the plurality of holes 3, 5, 7, 9, 11, and 13, so that the holes can be enlarged by cutting it out depending on the size of the electrode or the installation position of the electrode.

The implement 1 may further have a cut-out part 47 that connects a plurality of holes. When the cut-out part 47 exists, the implement 1 can be removed using the cut-out part after all of the electrodes are installed. As a result, it is possible to prevent the implement 1 from coming into contact with the patient for a long time. For example, when the implement 1 is transparent, the implement may be formed of plastic. When the implement 1 is in close contact with the patient for a long time, the patient will sweat and feel uncomfortable. For this reason, using the cut-out part 47, the implement can be easily removed from the patient. This is particularly effective when the implement 1 is a type worn by a patient, such as a T-shirt type.

As an example of the implement 1, the plurality of holes have a circular shape having a diameter of 1 mm or more and 15 mm or less, and markers of the holes are provided around the plurality of holes. The markers may exist so as to surround the holes. When it is difficult to visually recognize the holes, it is possible to easily and rapidly recognize the holes for installing the electrodes using the markers. For example, the plurality of holes may be smaller than the corresponding chest electrodes, and may be used to draw the corresponding chest electrode markers on the body surface through the respective holes. When the holes are small, it is possible to accurately determine the electrode positions advantageously.

As an example of the implement 1, the plurality of holes have a circular shape having a diameter of 30 mm or more and 60 mm or less. In this example, the holes can be used to mark the electrode positions. The plurality of holes may be larger than the corresponding chest electrodes, and may be used to install the corresponding chest electrodes on the body surface through the respective holes. When the hole is larger than the chest electrode, it is possible to take the electrocardiogram with this implement being applied. This improves convenience.

Advantageous Effects

It is possible to provide an implement for positioning electrocardiographic measurement electrodes, capable of rapidly determine the positions of the electrocardiographic electrodes depending on an individual patient.

DESCRIPTION OF EMBODIMENTS

Hereinafter, modes for embodying the present invention will be described with reference to the accompanying drawings. The embodiments described below are not intended to limit the present invention, but to encompass any appropriate modification of the following embodiments within the scope apparent to those skilled in the art.

Figure 1:
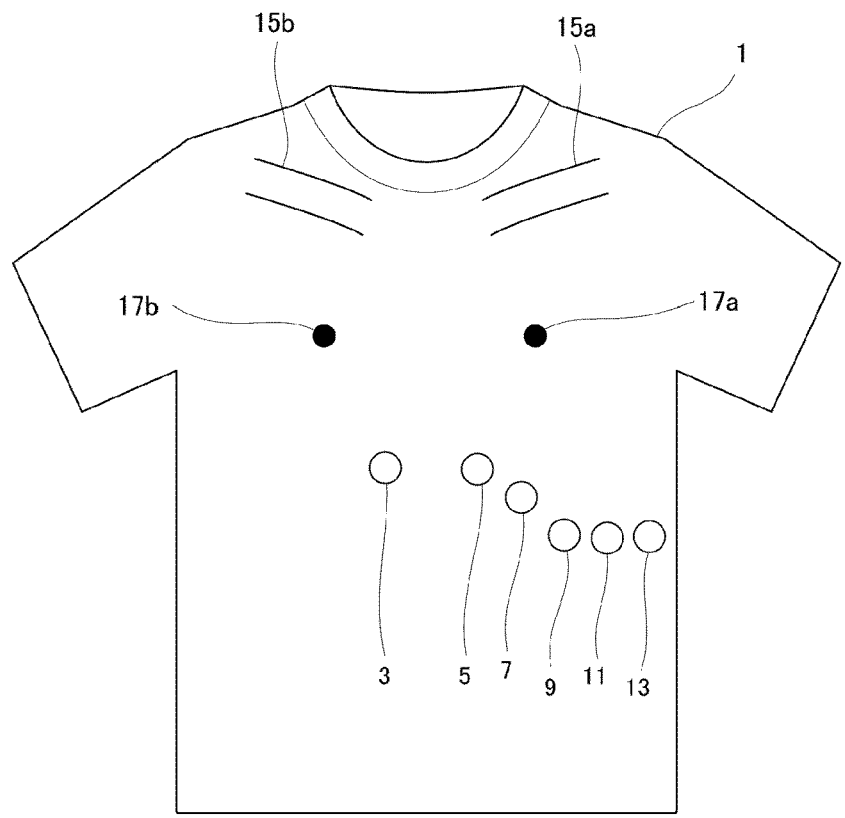
FIG. 1 is a conceptual diagram illustrating an example of an implement for positioning electrocardiographic measurement electrodes.

FIG. 1 is a conceptual diagram illustrating an example of an implement for positioning electrocardiographic measurement electrodes. The implement 1 for positioning electrocardiographic measurement electrodes can be achieved by an implement having a plurality of holes 3, 5, 7, 9, 11, and 13 corresponding to chest electrode positions. That is, positions of the electrodes are not fixed. Instead, holes for installing the electrodes are opened, and the electrodes are installed by using the holes as markers, so that positions of the electrodes can be rapidly determined depending on an individual patient. For this purpose, each hole preferably has a diameter equal to or larger than that of the employed electrocardiographic electrode. However, the hole may also be smaller than the electrode. In this case, for example, the implement 1 may be used to mark (draw) a marker of the electrode position on a body surface of the patient, and the marker may be used to install the electrode. The electrocardiographic measurement electrode is an element of an electrocardiographic measurement device used for measuring electrocardiogram. The electrocardiographic measurement device is well known in the art. In addition, the electrocardiographic measurement electrode is also well known in the art.

Figure 2:
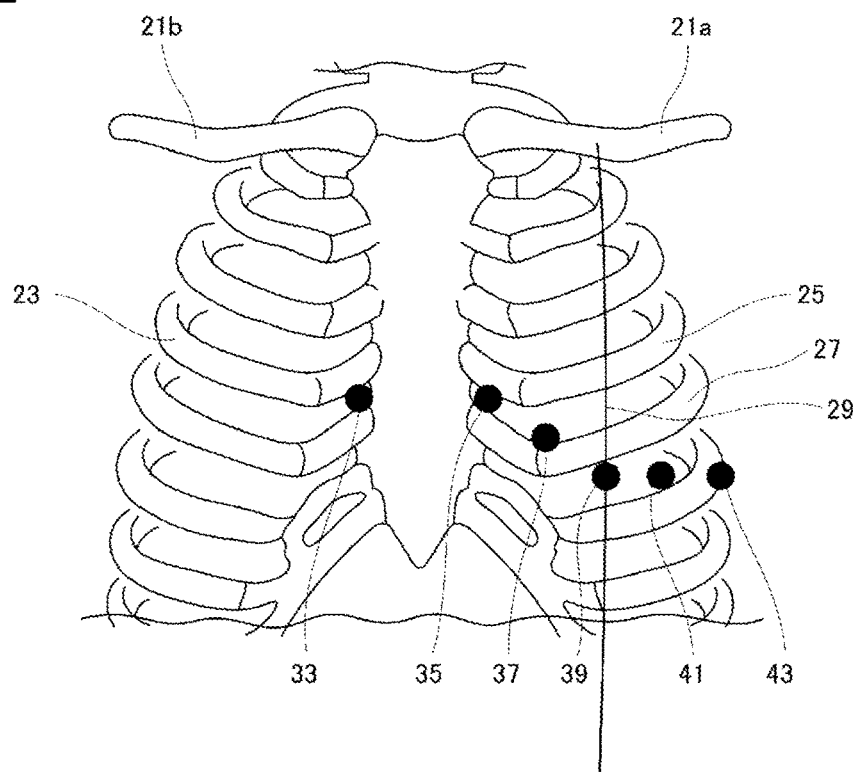
FIG. 2 is a conceptual diagram illustrating an example of chest electrode positions for twelve-lead electrocardiogram.

FIG. 2 is a conceptual diagram illustrating chest electrode positions of the twelve-lead electrocardiogram. The reference numerals "21a" and "21b" denote clavicles, "23" denotes a right rib, "25" and "27" denote left ribs, and "29" denotes a clavicle median. The reference numeral "33" denotes a first electrode region corresponding to the right fourth intercostal, "35" denotes a second electrode region corresponding to the left fourth intercostal, "37" denotes a third electrode region corresponding to the middle of the second and fourth electrode regions, "39" denotes a fourth electrode region placed in the left fifth intercostal on the clavicle median, "41" denotes a fifth electrode region placed in the left fifth intercostal on the anterior axillary line, and "43" denotes a sixth electrode region placed in the left fifth intercostal on the anterior axillary line. A plurality of holes 3, 5, 7, 9, 11, and 13 are provided in the positions corresponding to the chest electrode positions.

It is preferable that the implement 1 further has one or both of a clavicle marker 15a or 15b existing at a region corresponding to the clavicle portion and a mammilla marker 17a or 17b existing at a region corresponding to the mammilla portion. Using these markers, the implement can be installed at an appropriate position for a patient. The markers are, for example, printed on a front body section 19.

In particular, it is preferable that memories for the clavicle markers 15a and 15b are drawn together with standard clavicle positions. When the memories are drawn, it is possible to rapidly recognize how much a clavicle position of a target patient is deviated from the standard clavicle position. This is helpful when the electrode positions are very accurately adjusted.

It is preferable that the implement 1 has a transparent front body section 19. If the front body has a transparent section, the implement 1 can be arranged at an appropriate position depending on a patient. The entire front body may be transparent, or a periphery of the hole, a clavicle portion used to check the position of the hole, or the like may be transparent.

Figure 3:
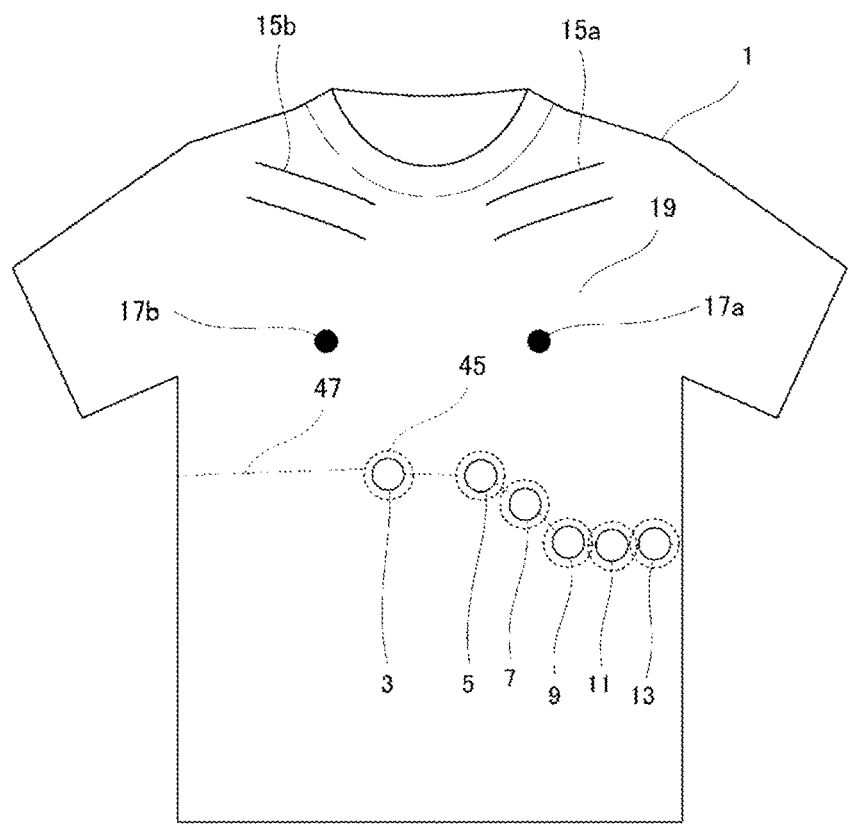
FIG. 3 is a conceptual diagram illustrating an example of a T-shirt type implement.

FIG. 3 is a conceptual diagram illustrating an example of a T-shirt type implement. As illustrated in FIG. 3, the front body section 19 preferably has a plurality of cut-out holes 45. It is preferable that the plurality of cut-out holes 45 exist, for example, so as to surround the plurality of hole portions 3, 5, 7, 9, 11, and 13 to allow the holes to be cut out and enlarged depending on the size of the electrode or the installation position of the electrode.

As illustrated in FIG. 3, the implement 1 may have a cut-out part 47 that connects a plurality of holes. When there is a cut-out part 47, the implement 1 can be removed by using the cut-out part after all of the electrodes are installed. As a result, it is possible to prevent the implement 1 from coming into contact with the patient for a long time. For example, when the implement 1 is transparent, the implement may be formed of plastic. When the implement 1 is in close contact with the patient for a long time, the patient will sweat and feel uncomfortable. For this reason, using the cut-out part 47, the implement can be easily removed from the patient with the electrodes being installed in the patient. This is particularly effective when the implement 1 is a type worn by a patient, such as a T-shirt type.

As an example of the implement 1, each of the plurality of holes has a circular shape having a diameter of 1 mm or more and 15 mm or less, and markers of the holes are provided around the plurality of holes. The markers may exist so as to surround the holes. When it is difficult to visually recognize the holes, it is possible to easily and rapidly recognize the holes for installing the electrodes using the markers. For example, the plurality of holes may be smaller than the corresponding chest electrodes, and may be used to draw the corresponding chest electrode markers on the body surface through the respective holes. When the holes are small, it is possible to accurately determine the electrode positions advantageously. When the hole is smaller than the corresponding chest electrode, this means that the chest electrode is not allowed to pass through the corresponding hole, or the area of the hole is smaller than that of the corresponding chest electrode.

As an example of the implement 1, each of the plurality of holes has a circular shape having a diameter of 30 mm or more and 60 mm or less. In this example, the holes can be used to mark the electrode positions. The plurality of holes may be larger than the corresponding chest electrodes, and may be used to install the corresponding chest electrodes on the body surface through the respective holes. When the hole is larger than the chest electrode, it is possible to take the electrocardiogram with this implement being applied. This improves convenience. When the hole is larger than the corresponding chest electrode, this means that the chest electrode is allowed to pass through the corresponding hole, or the area of the hole is larger than that of the corresponding chest electrode.

Figure 4:
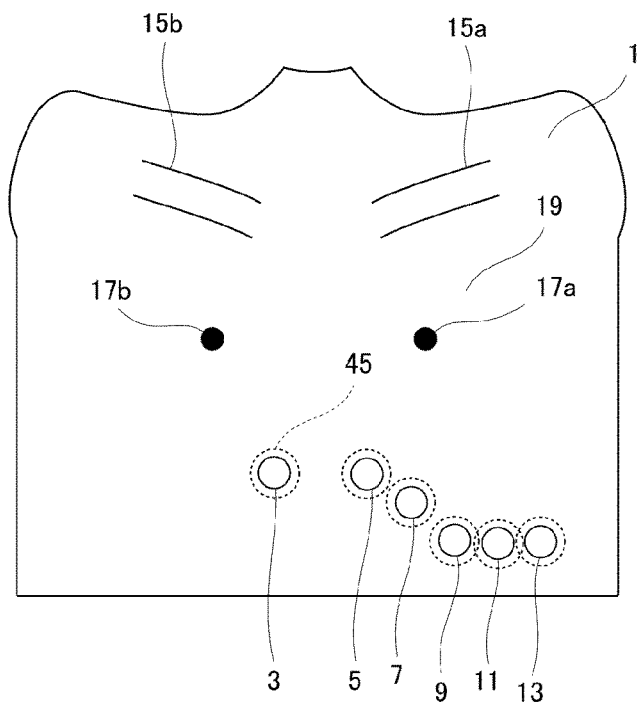
FIG. 4 is a conceptual diagram illustrating an example of an apron-type implement.

FIG. 4 is a conceptual diagram illustrating an example of an apron-type implement. The shape of the implement is not limited as long as the position of the electrode can be guided. The implement may be a T-shirt type as illustrated in FIG. 1, an apron type as illustrated in FIG. 4, or any other type. In addition, a plurality of types of implements may be prepared depending on a patient's body size such as XS, S, M, L, and XL, or gender such as men or women, and the electrode positions may be more appropriately adjusted by using the implement that suits the patient. In any case, it is possible to more rapidly and accurately install the electrodes, compared to a case where the electrodes are installed without preparing anything.

The implement for positioning electrocardiographic measurement electrodes can be manufactured, for example, as follows. A T-shirt or apron that serves as a base for the plurality of types of implements described above is prepared. At least the entire front body or the area of the front body that covers the electrode position and the clavicle is made to be transparent. Standard electrode positions for each size are obtained in advance, and the holes are punched out in the standard electrode positions. In addition, the areas that serve as markers are printed. In addition, a cutting line is prepared to allow a necessary part to be cut out during or after use. Note that a base material may be prepared as described above, and may be processed into a final form of the implement such as a T-shirt or apron. For example, when electrocardiogram is measured, this implement is worn by a patient and allows an operator to install the electrodes by using the holes as references. As a result, it is possible to rapidly and accurately install the electrodes.

INDUSTRIAL APPLICABILITY

The present invention is applicable to medical instrument fields. References Signs and Numerals 1 implement for positioning electrocardiographic measurement electrodes
3, 5, 7, 9, 11, 13 hole
15a, 15b clavicle marker
17a, 17b mammilla marker
19 front body section
45 cut-out hole
47 cut-out part

What is claimed is:

1. An implement for electrocardiogram positioning, comprising:
   the implement adapted to be worn by a wearer;
   a plurality of holes along the implement corresponding to a plurality of chest electrode positions, wherein each of the plurality of chest electrodes are configured to pass through a respective hole of the plurality of holes to position the plurality of chest electrodes against a body surface of the wearer;
   a plurality of cut-out holes along the implement, wherein each of the plurality of cut-out holes is configured to have a circular shape and surrounds a respective hole of the plurality of holes, and wherein each of the plurality of cut-out holes is configured to be cut to enlarge the respective hole of the plurality of holes; and
   a cut-out part extending along the implement and across all the plurality of holes, wherein the cut-out part is configured to cut through the plurality of holes of the implement to separate the implement into pieces to remove the implement from the wearer after the placement of the plurality of chest electrodes against the body surface of the wearer.

2. The implement according to claim 1, further comprising:
   one or both of a clavicle marker existing in a region corresponding to a clavicle portion and a mammilla marker existing in a region corresponding to a mammilla portion.

3. The implement according to claim 1, wherein the implement comprises a transparent front body section.

4. The implement according to claim 1, wherein
   the plurality of holes have a circular shape having a diameter of from 1 mm to 15 mm, both inclusive, and
   markers of the holes are provided around the plurality of holes.

5. The implement according to claim 1, wherein the plurality of holes are smaller than corresponding chest electrodes, and the implement is configured to be used to draw markers for the corresponding chest electrodes on the body surface through the respective holes.

6. The implement according to claim 1, wherein
   the plurality of holes have a circular shape having a diameter of from 30 mm to 60 mm, both inclusive.

7. The implement according to claim 1, wherein the plurality of holes are larger than the corresponding chest electrodes, and the implement is used to position the corresponding chest electrodes on the body surface through the respective holes.

8. The implement according to claim 1, wherein the implement is an apron-type implement.

9. The implement according to claim 8, wherein the implement further comprises a transparent front body.

10. The implement according to claim 1, wherein a clavicle portion in the implement is transparent.

11. The implement according to claim 1, further comprising a pair of clavicle markers along the implement corresponding to a pair of clavicles of the wearer and a pair of mammilla markers along the implement corresponding to mammilla portion of the wearer.

* * * * *